United States Patent [19]  [11] 4,026,770
Scharfe et al.  [45] May 31, 1977

[54] PROCESS FOR REMOVING 1,4-NAPHTHOQUINONE FROM PHTHALIC ANHYDRIDE

[75] Inventors: Gerhard Scharfe; Rupert Wenzel, both of Leverkusen; Wolfgang Biedermann, Krefeld, all of Germany

[73] Assignee: Bayer Aktiengesellschaft, Leverkusen, Germany

[22] Filed: Oct. 29, 1975

[21] Appl. No.: 627,155

[30] Foreign Application Priority Data

Nov. 13, 1974 Germany ............................ 2453745

[52] U.S. Cl. .............................. 203/29; 260/346.7
[51] Int. Cl.$^2$ ...................................... C07D 307/89
[58] Field of Search ................... 260/346.7, 396 R; 203/29, 30

[56] References Cited

FOREIGN PATENTS OR APPLICATIONS 1,179,443  1/1970  United Kingdom ............ 260/346.7

Primary Examiner—Henry R. Jiles
Assistant Examiner—Bernard Dentz
Attorney, Agent, or Firm—Burgess, Dinklage & Sprung

[57] ABSTRACT

1,4-naphthoquinone is removed from phthalic anhydride by heating with elementary sulfur at temperatures in the range of from 200° to 300° C.

6 Claims, No Drawings

PROCESS FOR REMOVING 1,4-NAPHTHOQUINONE FROM PHTHALIC ANHYDRIDE

BACKGROUND

The present invention relates to a process for removing 1,4-naphthoquinone from phthalic anhydride.

It is known from Ullmann, volume 13, pages 720 – 721, that phthalic anhydride which has been obtained by gas phase oxidation of naphthalene can contain small quantities of 1,4-naphthoquinone. Further, it is known from this publication that 1,4-naphthoquinone can be removed by subjecting the crude phthalic anhydride to a heat treatment with concentrated sulphuric acid. After the heat treatment, the excess sulphuric acid is neutralised by adding chalk. Distillation then gives a phthalic anhydride which has been freed from 1,4-naphthoquinone. The disadvantage of this process is the corrosion occasioned by the presence of sulphuric acid and the formation of solid residues during distillation, occasioned by the addition of chalk, so that this process can for practical purposes only be carried out discontinuously.

SUMMARY

According to the present invention there is provided a process for removing 1,4-naphthoquinone from phthalic anhydride in which phthalic anhydride containing 1,4-naphthoquinone is subjected to a heat treatment with elementary sulphur at a temperature of from 200° to 300° C.

DESCRIPTION

Commercial sulphur can be used as the sulphur for this process.

Processes which give phthalic anhydride containing 1,4-naphthoquinone are in themselves known. For example, the gas phase oxidation of naphthalene (see the Ullmann literature reference cited above) and the oxidation of naphthalene to 1,4-naphthoquinone and phthalic anhydride, reaction of the 1,4-naphthoquinone with butadiene to give tetrahydroanthraquinone and subsequent conversion of the tetrahydroanthraquinone to anthraquinone. The phthalic anhydride thereby produced also contains small amounts of 1,4-naphthoquinone. For use with the scope of the process according to the invention, the content of 1,4-naphthoquinone in the phthalic anhydride to be purified is in principle not critical. In general however, occasioned by the type of process used to manufacture the phthalic anhydride, the content of 1,4-naphthoquinone is less than 2% by weight, for example 0.2 to 0.5% by weight.

In carrying out the process according to the invention, the procedure generally followed comprises taking the liquid phthalic anhyride containing 1,4-naphthoquinone, adding the sulphur in the solid or liquid form, ensuring homogeneous mixing of sulphur into the phthalic anhydride, for example by stirring, then heating the resulting mixture of phthalic anhydride, containing 1,4-naphthoquinone, and sulphur, to a temperature of from 200 to 300° C, preferably 220 – 280° C, and particularly preferentially 240°– 260° C, and maintaining the mixture for some time at the elevated temperature. The reaction time can vary within wide limits. Suitable reaction times have in general proved to be from 1 to 10 hours, though 2 to 4 hours can be entirely adequate. The sulphur is in general added in an amount of from 0.1 to 1 part by weight of sulphur per part by weight of 1,4-naphthoquinone. Amounts of 0.2 to 0.5 parts by weight of sulphur per part by weight of 1,4-naphthoquinone are preferred.

The reaction of the impure phthalic anhydride with elementary sulphur can be carried out under normal pressure, reduced pressure or elevated pressure. Furthermore, the reaction can be carried out continuously or discontinuously. Where it is carried out discontinuously, the crude phthalic anhydride and sulphur, in a solid or liquid form, can be taken and then heated for 1 to 10 hours at temperatures of 200° to 300° C. The process according to the invention can be carried out continuously in various ways, for example in a stirred kettle cascade or a tube reactor (a long length of pipe).

Pure phthalic anhydride which is free from 1,4-naphthoquinone can then be obtained from the reaction product of the heat treatment, by distillation, in any conventional manner. The following Examples illustrate the invention.

EXAMPLES 1 TO 4

Mixtures of phthalic anhydride, 1,4-naphthoquinone and elementary sulphur were made up and weighed out into glass bomb tubes. The bomb tubes were sealed and heated at 250° C for 3 hours. After cooling, the content of naphthoquinone in the reaction product was determined by gas chromatography. The following results were obtained:

Table 1

| Starting product: | synthetic mixture of 99% of phthalic anhydride and 1% by weight of 1,4-napthoquinone | | | | |
|---|---|---|---|---|---|
| Example No. | — | 1 | 2 | 3 | 4 |
| Added sulphur in parts by weight/ part by weight of 1,4-naphthoquinone employed | 0 (for comparison) | 0.05 | 0.1 | 0.5 | 1.0 |
| Content of 1,4-naphthoquinone in the product after heat treatment, in ppm by weight. | 6,000 | 200 | <5 | <5 | <5 |

EXAMPLE 5

A commercial grade of phthalic anhydride originating from the gas phase oxidation of naphthalene and containing 0,2% by weight of 1,4-naphthoquinone was introduced continuously into a stirred kettle, together with 0.1% by weight of sulphur, relative to phthalic anhydride, and was heat-treated in the kettle at 250° C with an average residence time of 1 hour. Thereafter the reaction mixture was passed through a finishing tube reactor (a long length of pipe) in which a further heat treatment at 250° C is carried out with a residence time of 2 hours. The product thus obtained is passed into a distillation column operated continuously under reduced pressure. 97% of the phthalic anhydride employed was obtained as a distillate. The content of naphthoquinone in the distillate was less than 5 ppm.

What is claimed is:

1. Process for removing 1,4-naphthoquinone from phthalic anhydride which comprises heating phthalic anhydride containing 1,4-naphthoquinone with elementary sulphur at a temperature of from 200° to 300°

C. and thereafter distilling the reaction product from the heat treatment.

2. Process of claim 1 wherein from 0.1 to 1 part by weight of sulphur is employed per part by weight of 1,4-naphthoquinone.

3. Process of claim 1 wherein the heat treatment is carried out at a temperature of from 240° to 260° C.

4. Process of claim 1 wherein the heat treatment is continued for a period of from 1 to 10 hours.

5. A process for chemically removing 1,4-naphthoquinone from phthalic anhydride containing the same which comprises adding to the phthalic anhydride containing 1,4-naphthoquinone, elementary sulphur and heating the resultant mixture at a temperature of from 200° to 300° C.

6. Process of claim 5 wherein the reaction product from the heat treatment is distilled.

* * * * *

UNITED STATES PATENT AND TRADEMARK OFFICE
CERTIFICATE OF CORRECTION

PATENT NO. : 4,026,770
DATED : May 31, 1977
INVENTOR(S) : Gerhard Scharfe et al

It is certified that error appears in the above-identified patent and that said Letters Patent are hereby corrected as shown below:

Column 1, line 47, "with" should read -- within --.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*